United States Patent
Bettega et al.

(12)
(10) Patent No.: US 6,213,769 B1
(45) Date of Patent: Apr. 10, 2001

(54) DEVICE FOR DETERMINING A MOVEMENT BETWEEN TWO DENTAL CAST PROFILE USING AN X-RAY SCANNER

(75) Inventors: Georges Bettega; Philippe Cinquin; Stéphane LaVallee, all of Grenoble; Bernard Raphael, Saint Ismier, all of (FR)

(73) Assignee: Universite Joseph Fourier, Grenoble (FR)

( * ) Notice: Subject to any disclaimer, the term of this patent is extended or adjusted under 35 U.S.C. 154(b) by 0 days.

(21) Appl. No.: 09/331,468
(22) PCT Filed: Dec. 12, 1997
(86) PCT No.: PCT/FR97/02383
  § 371 Date: Aug. 30, 1999
  § 102(e) Date: Aug. 30, 1999
(87) PCT Pub. No.: WO98/27892
  PCT Pub. Date: Jul. 2, 1998

(30) Foreign Application Priority Data

Dec. 20, 1996 (FR) .................................. 96 16066

(51) Int. Cl.⁷ ................................................ A61C 19/045
(52) U.S. Cl. ............................................. 433/56; 433/69
(58) Field of Search ............................ 433/54, 55, 56, 433/196, 69

(56) References Cited

U.S. PATENT DOCUMENTS

| 4,409,616 | * | 10/1983 | Ledley . | |
| 4,859,181 | * | 8/1989 | Neumeyer | 433/69 |
| 5,257,932 | * | 11/1993 | Leinfelder et al. | 433/56 |
| 5,340,309 | * | 8/1994 | Robertson . | |
| 5,743,732 | * | 4/1998 | Watson | 433/69 |
| 5,905,658 | * | 5/1999 | Baba | 433/69 |

FOREIGN PATENT DOCUMENTS

| 93 00 365 | * | 3/1993 | (DE) . |
| 0 373 077 | * | 6/1990 | (EP) . |
| 0 375 982 | * | 7/1990 | (EP) . |

OTHER PUBLICATIONS

Katsuyuki et al., Measurments of ental Cast Profile and Three Dimensional Tooth Movement During Orthodontic Treatment, IEEE Transactions On Biomedical Engineering, vol. 38, No. 4, New York, pp. 360–365, Apr. 1991.*

* cited by examiner

*Primary Examiner*—Todd E. Manahan
(74) *Attorney, Agent, or Firm*—Arthur L. Plevy; Buchanan Ingersoll PC

(57) ABSTRACT

A system for simulating an orthognatic surgery action, including an X-ray scanner, a device of three-dimensional localization of relative positions of dental castings, each associated with a unit locatable in position and orientation by the localization device, and an image processing system for combining tomographic images provided by the scanner with positioning data provided by the localization device to obtain three-dimensional images.

15 Claims, 2 Drawing Sheets

DEVICE FOR DETERMINING A MOVEMENT BETWEEN TWO DENTAL CAST PROFILE USING AN X-RAY SCANNER

BACKGROUND OF THE INVENTION

1. Field of the Invention

The present invention relates to devices used in orthognatic surgery interventions or in the preparation thereof. Such interventions are surgery interventions of repair, in particular, of a mispositioning of the jaws with respect to each other. An orthognatic surgery intervention especially consists of performing osteotomies of the maxilla and/or of the mandible to reposition them correctly with respect to the rest of the skull by recreating a defective bite.

2. Discussion of the Related Art

The preparation of such a surgery intervention requires implementing orthodontic and radiological techniques.

A mandibular casting and a maxillary casting providing the respective implantations of the patient's teeth in the respectively mandibular and maxillary bone segments are first performed. The castings, generally made of plaster, are used to simulate the relative displacement which has to be applied to the jaws to recreate the bite. To enable the surgeon to respect these simulated relative positions, a plate comprising, on each of its surfaces, tooth-prints of the two castings is made with the dental castings. Such a plate, called an interscupidation plate, is used to maintain the castings or the jaws in relative positions where the teeth are in occlusion.

Since the surgical intervention generally includes osteotomies of both jaws, two interscupidation plates are generally made from the dental castings, in addition to a so-called initial interscupidation plate linking the two jaws in their occlusion position before the intervention.

A so-called intermediary plate determines the foreseeable displacement of the maxilla with respect to the mandible when said mandible is in its original (preoperative) position. This plate enables the surgeon to place the maxilla back on the skull in the desired definitive position before intervening on the mandible. A so-called definitive plate determines the occlusion objective to be surgically achieved and is thus used to correctly position the mandible on the skull by setting the position of the mandible with respect to the previously replaced maxilla.

The preparation of the surgical operation also uses a profile radiography of the patient enabling, in particular, performing an approximate simulation of the operative action.

This simulation is performed manually from a tracing paper placed on the radiography. For example, the contours of the mandible are first drawn. The tracing paper is then moved to approximately reproduce thereon the desired postoperatory occlusion, after which the maxillary contours are drawn. The maxillomandibular assembly drawn on the tracing paper is then moved in one block while respecting cephalometric standards, labial ratios, as well as other criteria known for this type of intervention. The direction and amplitude of the jaw displacements are thus radiologically and approximately defined. The results of this simulation are compared and adjusted according to the relative motion of the mandible and of the maxilla envisaged by means of the interscupidation plates.

The actual simulation of an orthognatic surgery intervention is thus performed essentially manually. Further, this simulation is only done in two dimensions based on a plane profile view of the skull.

The development of scanners associated with image processing systems enables obtaining three-dimensional views of a patient's skull. Such systems would be particularly useful to perform a three-dimensional simulation of an orthognatic surgery intervention. In particular, it is known to isolate from one another different portions of the three-dimensional images reconstructed from scanner cross-sections. Thus, a portion corresponding to the maxilla and a portion corresponding to the mandible could be isolated from the rest of the skull. This would enable simulating, by means of the image processing system, relative displacements of these elements with respect to one another. However, the sole use of such three-dimensional image processing systems for a simulation of an orthognatic surgery intervention remains up to now impossible for several reasons.

First, the accuracy of a scanner is incompatible with the accuracy requirement of a bite. Indeed, the jaw positioning accuracy required for the bite is on the order of one tenth of a millimeter while the minimum pitch between two scanner tomographies ranges from approximately two to five millimeters. The respective initial positions of the mandible and of the maxillary thus cannot be precisely reproduced by means of the scanner.

Second, teeth amalgams (fillings) create artifacts which appear as blurred spots on the scanner images. It is thus impossible to plot, on a three-dimensional view, the exact position of the teeth based on the scanner images to obtain the bite.

A technique of preparation and assistance of an operatory action in orthognatic surgery using a scanner is however known. This technique consists of affixing three titanium screws on the patient's maxillary. A resin model of the skull is then made based on scanner cross-sections of the patient's skull. Since the screws appear on the scanner views, they are reproduced on the model. The screws are used to position with respect to the skull a metal frame for receiving a final interscupidation plate. This plate is made based on maxillary and mandibulary dental castings taken on the patient. Once the castings are made, the maxillary is cut-off from the resin model to be replaced with the corresponding casting. The maxillary casting is attached to the model in the desired definitive position. Then, the mandible is cut-off from the model to be replaced with a casting previously made on the patient.

The position of the mandibular casting is given, with respect to the maxillary, by the interscupidation plate which is then rigidly coupled to the metal frame forming a system of transfer of the plate position between the model and the patient. The frame is then brought back on the patient in the position defined by the three maxillary screws and is attached to the patient's skull by two additional screws. The position of the transfer system being now fixed by these two screws, the osteotomy of the maxillary, which is correctly repositioned by means of the interscupidation plate which is rigidly coupled to the transfer system, is performed. Then, the osteotomy of the mandible is performed, and said mandible is correctly positioned by means of the interscupidation plate.

Such a technique has several drawbacks. On the one hand, it requires an additional surgical intervention to place the screws in the patient's mouth. On the other hand, it requires making a resin model of the skull, which is particularly costly. Further, the simulation is performed, empirically, by means of the resin model and does not enable taking account of cephalometric standards based on accurate data.

SUMMARY OF THE INVENTION

The present invention aims at providing a novel system for three-dimensional simulation of orthognatic surgery interventions.

To achieve this object, the present invention provides an interscupidation plate for defining an occlusion between two, respectively mandibular and maxillary, dental castings, including, protruding from its front end, a guide mark visible by means of an X-ray scanner and adapted to defining a first referential in three-dimensional images reconstructed from scanner views.

According to an embodiment of the present invention, the guide mark has at least two non-parallel rectilinear edges.

According to an embodiment of the present invention, the guide mark is formed of at least two rods connected to the interscupidation plate and forming together a determined angle.

According to an embodiment of the present invention, the rods are hollow and open at their distal end from the interscupidation plate.

The present invention also relates to a device for determining a three-dimensional displacement between first and second relative positions of two dental castings, including a first unit, associated with a first dental casting and locatable in position and orientation by a localization device, a second unit, associated with a second dental casting and locatable by the localization device, a first interscupidation plate defining the first relative position between the two castings, the first plate being locatable by the localization device, means for storing the position of the second unit with respect to the first unit when the relative position of the castings is determined by the first interscupidation plate, means for defining the second relative position of the castings, and calculation means adapted to determining the three-dimensional displacement of the second unit between the two positions.

According to an embodiment of the present invention, the means for defining of the second relative position of the castings are formed of a second interscupidation plate, the device further including means for storing of the relative position of the second unit with respect to the first unit when the position of the castings is determined by the second interscupidation plate, and calculation means adapted to determining the three-dimensional displacement of the second unit between the two positions.

According to an embodiment of the present invention, the means for defining the second relative position of the castings comprise a device for digitizing the surfaces of the castings and image processing means.

According to an embodiment of the present invention, the localization device is formed of an optical locator, the locatable units including infrared-emitting diodes.

According to an embodiment of the present invention, the localization device is formed of several video cameras associated with image processing means, the locatable units being formed of graphic patterns.

The present invention further relates to a system for simulating of an orthognatic surgery action, including an X-ray scanner, a device of three-dimensional localization of relative positions of dental castings, each associated with a unit locatable in position and orientation by the localization device, and an image processing system for combining tomographic images provided by the scanner with positioning data provided by the localization device to obtain three-dimensional images.

According to an embodiment of the present invention, the localization device is part of a device for determining a three-dimensional displacement between first and second relative positions of the two dental castings.

According to an embodiment of the present invention, a first position is determined by a first interscupidation plate.

According to an embodiment of the present invention, a relation between the first and second referentials is determined from an additional unit of a reference element adapted to being mechanically associated to the guide mark of the first interscupidation plate.

According to an embodiment of the present invention, the guide mark of the first interscupidation plate is rigidly coupled with a third locatable unit which defines a second referential associated with the first plate.

The foregoing objects, features and advantages of the present invention will be discussed in detail in the following non-limiting description of specific embodiments in connection with the accompanying drawings.

DETAILED DESCRIPTION

A feature of the present invention is to associate, with an image processing system providing three-dimensional images from an X-ray scanner, a device for determining a three-dimensional displacement between first and second relative positions of two dental castings. The scanner images and the positions and orientations of the castings determined by the device are combined in an image processing system to obtain an accurate three-dimensional simulation system.

The present invention will be described hereafter based on an example of a practical case implementing the simulation system according to the present invention. It should however be noted that the succession of steps indicated hereafter may be modified.

Two, respectively maxillary and mandibular, dental castings reproducing the respective positions of the teeth in each jaw are first made.

A first, so-called initial interscupidation plate corresponding to the mandibular position in usual occlusion on the maxilla is also formed. This plate is generally formed by taking a mouth-print of the patient.

Figure 1:
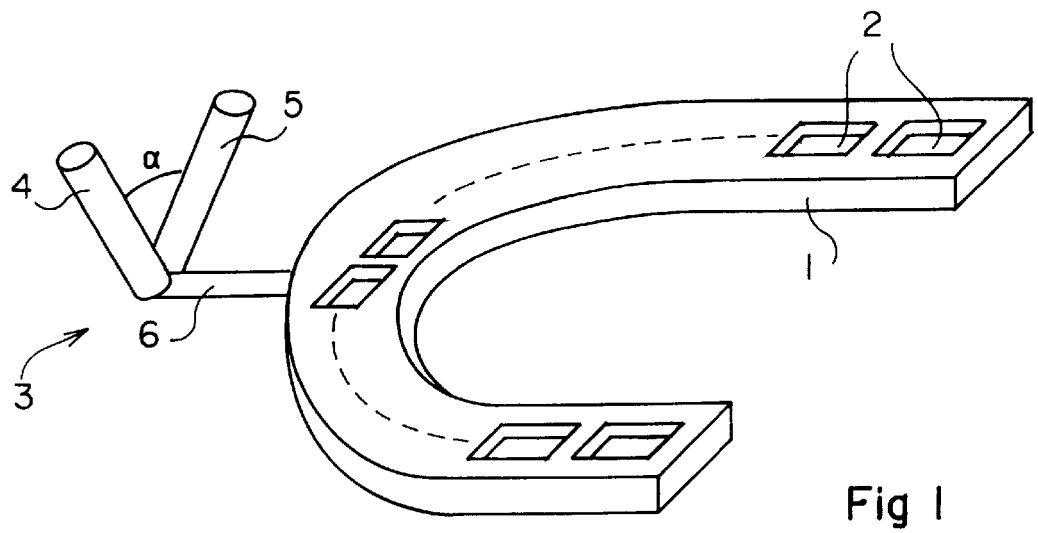
FIG. 1 shows an embodiment of an interscupidation plate according to the present invention.

FIG. 1 shows an embodiment of an initial interscupidation plate according to the present invention.

Such an interscupidation plate 1 is made by conventional means. Plate 1 includes, on each of its surfaces, prints 2 of the teeth of both jaws. Prints 2 are not through prints but are sufficiently deep for the teeth reconstituted on the castings to be in occlusion position when plate 1 is inserted between the two dental castings. In FIG. 1, a few prints 2 only have been shown.

According to the present invention, interscupidation plate 1 bears a physical guide mark 3. The function of guide mark 3 is to designate a three-dimensional referential, in images reconstructed from cross-sections taken with a scanner (not shown), which is locatable, directly or indirectly, by an external device (not shown in FIG. 1), called a locator, of determination of the relative positions and orientations of the castings to combine, within the image processing system, the scanner images with position and orientation data provided by the locator. The locator may be a stereo-vision system, an optical sensor of diode positions, an ultrasonic system, an electromagnetic sensor, or others.

Preferably, guide mark 3 protrudes from the front end of plate 1 to be accessible when plate 1 is associated with the dental casting.

In the example shown in FIG. 1, guide mark 3 is formed of two rods 4 and 5 included in a plane approximately perpendicular to the plane of plate 1. Rods 4 and 5 are supported, by one of their respective ends, by a support 6. Support 6 is formed, for example, of a rod approximately coplanar to plate 1, protruding from the front of plate 1. Rods 4 and 5 define an angle α together, starting from support 6.

As an alternative, not shown, rods 4 and 5 may be supported, by one of their respective ends, directly by plate 1. In this case, the plane containing rods 4 and 5 is inclined forward with respect to the plane perpendicular to the plane of plate 1, to avoid the patient's nose when plate 1 is placed between the patient's teeth. Of course, this alternative may be combined with the use of a support 6 protruding from plate 1, the inclination angle of the plane that contains rods 4 and 5 being then adapted to the overhang introduced by support 6.

A feature of a guide mark 3 according to the present invention is that it is formed of a material which generates no artifact in a scanner visualization. For example, rods 4 and 5 and the possible support 6 are made of aluminum or of rigid plastic visible by an X-ray scanner.

According to another embodiment not shown, guide mark 3 is formed of any geometric shape having at least two rectilinear non-parallel edges, visible by a scanner. It may be, for example, a star-shaped plate supported by a support protruding from the front portion of plate 1.

Another feature of guide mark 3 according to the present invention is that it is also used to locate plate 1 by means of a three-dimensional localization device, or locator. For this purpose, guide mark 3 forms, by itself, a mark visible by the locator as will be described hereafter.

Once the initial interscupidation plate has been made, a series of tomographic cross-sections of the skull are performed by means of the scanner with this plate positioned between the jaws. A three-dimensional modeling of the skull and jaws is thus obtained by means of the image processing system.

Since rods 4 and 5 are not parallel, a readjustment processing between the points of rods 4 and 5 present in several images which correspond to parallel cross-sections and a known geometrical model of these rods enables knowing the position and orientation of a referential defined by the rods and associated with plate 1, that is, of guide mark 3, in the referential of the images provided by the processing system.

It should be noted that guide mark 3 may include a greater number of rods, for example, three non-coplanar rods non-parallel two by two, to more reliably and accurately define a referential.

To enable simulating the surgical intervention based on the reconstructed three-dimensional images, the relative three-dimensional displacement to be applied to the respective maxilla and mandible must be transferred into the image processing system.

Figure 2:
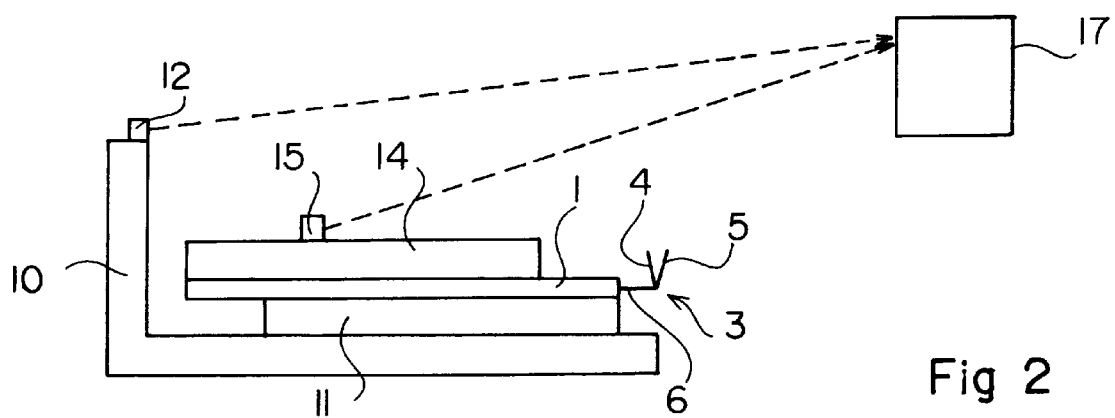
FIGS. 2 and 3 schematically illustrate a first embodiment of a device of determination of a three-dimensional displacement between two dental castings according to the present invention.
Figure 3:
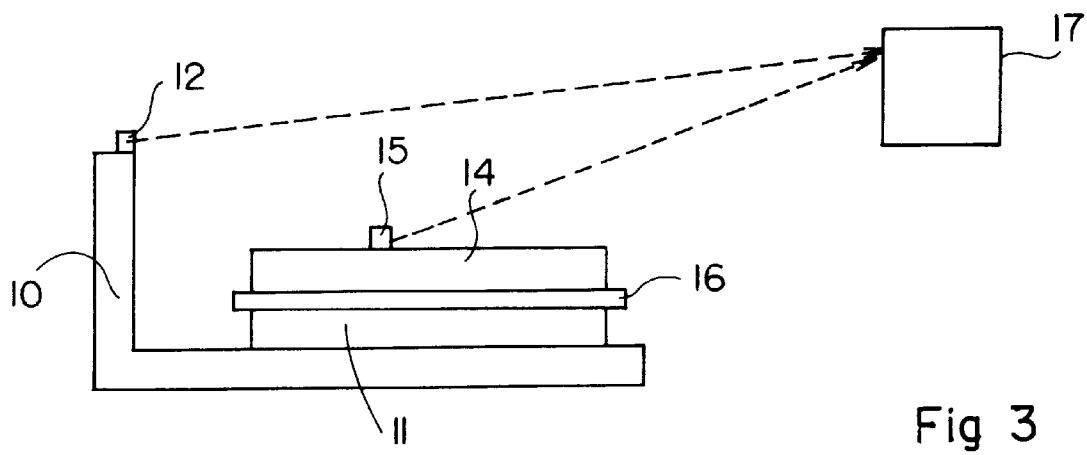

For this purpose, a displacement determination device, a first embodiment of which is described hereafter in relation wit FIGS. 2 and 3, is used.

According to this first embodiment of the present invention, a second so-called final interscupidation plate corresponding to the desired occlusion objective is made based on the dental castings.

This final interscupidation plate may be formed, conventionally, by placing the two dental castings on an adjustable articulator to have some dental anatomic marks taken on the mandible casting coincide with other marks taken on the maxilla casting, according to the desired postoperatory objective.

The final interscupidation plate may also be formed, according to the present invention, based on a digitization of the respective casting surfaces by designating reference marks on these surfaces in a computer system. A motor-driven articulator may then be used to place the two castings in the desired final position and then more accurately form the final plate. The digitization of dental surfaces is a known technique.

According to the described embodiment, an optical locator enabling accurate definition of the respective positions and orientations of the mandible and maxilla castings, is used. Such an optical locator is known in prior art. It generally uses units equipped with infrared-emitting diodes, rigidly coupled with the elements to be located. The respective positions and orientations of the units are detected by means of a device 17 provided with three bars (not shown) of charge transfer photosensitive elements (CCD) and cylindrical lenses which project the image of the infrared-emitting diodes on these bars. The bar disposition, one horizontal and two vertical, enables defining the position of any point present in the field of sensor 17 with a good accuracy, generally 0.1 mm in the front plane of the sensor and 0.15 nm in depth. The association of the respective positions of the diodes of a same unit (generally two pairs of diodes in perpendicular directions) enables determining the position and orientation of the element associated with the unit.

According to the present invention, the device of determination of the three-dimensional displacement between the first and second relative positions of the two dental castings, respectively attached on the initial and final interscupidation plates, includes a support 10 of reception of the mandible casting 11, the position of casting 11 being fixed with respect to support 10. Support 10 or casting 11 is associated with a first infrared-emitting diode unit 12. First unit 12 defines a three-dimensional referential, associated with mandible casting 11 and fixed with respect to sensor 17.

In a first step (FIG. 2), initial interscupidation plate 1 and maxillary casting 14 are placed in occlusion on casting 11. Maxillary casting 14 is provided with a localization unit 15 defining a three-dimensional referential associated with the maxillary casting.

A localization of units 12 and 15 is performed by the optical locator. This localization provides the position and orientation of the units in a referential associated with sensor 17, and thus with the locator. The relative positions of the two referentials respectively associated with the mandible casting and with the maxilla casting in the usual occlusion position are then determined by calculation means. The relation (transfer matrix) between the referential associated with the mandible casting and the referential associated with the maxilla casting in its initial position, as well as the respective relations of these two referentials with the referential associated with sensor 17, can thus be determined.

In a second step illustrated in FIG. 3, initial interscupidation plate 1 is replaced with the final interscupidation plate made from the dental castings. Final interscupidation plate 16 defines the relative position of the mandible and maxilla castings in the desired occlusion objective. By performing a second series of measurements with the optical locator, the respective positions and orientations of units 12 and 15, and thus of the mandible and maxilla castings in the desired final position are obtained. The relation between the new referential associated with maxilla casting 14 and the referential associated with mandible casting 11 which has not changed can thus be determined.

Finally, the relation (transfer matrix) between the two, respectively initial and final, referentials of the maxilla casting, is determined based on the respective relations between the referential of casting 11 and the initial and final referentials of casting 14. The three-dimensional displacement between the respective initial and final positions of maxilla casting 14 with respect to mandible casting 11 is thus known.

To enable associating the position information with the scanner cross-sections, the relation between the referential associated with guide mark 3 and the referential associated with sensor 17 is determined.

Figure 4:
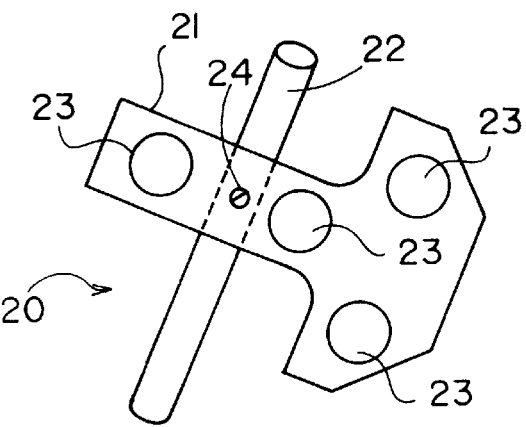
FIG. 4 shows an embodiment of a reference element according to the present invention associated with a guide mark visible by a scanner of an interscupidation plate such as shown in FIG. 1.
Figure 4:
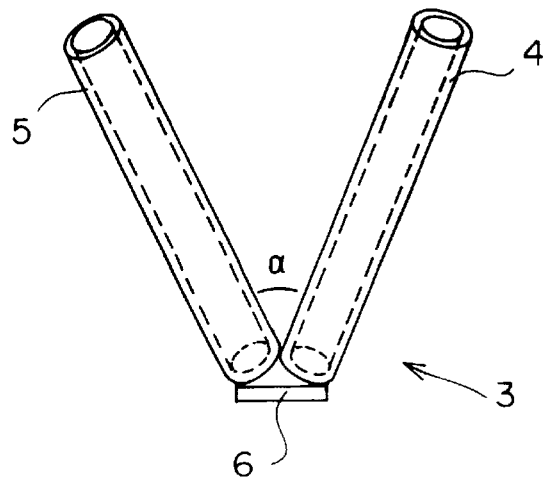

This determination of the transfer matrix between these two referentials is, according to the described embodiment, performed in an additional step by means of a reference element, an embodiment of which, intended for a guide mark 3 such as previously described, is shown in FIG. 4.

Reference element 20 is formed of an additional unit 21 of infrared-emitting diodes 23, rigidly coupled, for example, by one or several screws 24, with a rectilinear element 22 of connection with a rod 4 or 5 of guide mark 3. For example, each rod 4 or 5 is hollow and open at its free end and the connection element is formed of a rod 22 intended for engaging into one of rods 4 or 5. Rod 22 has, when engaged in a rod 4 or 5, two degrees of liberty (sliding and rotation) with respect thereto. Unit 21 defines a three-dimensional referential associated with rod 22.

The coordinates of two points arbitrarily chosen along rod 22 are first determined in its referential by means of sensor 17. Rod 22 is then engaged into one of the rods (for example, 4) of guide mark 3 and the respective positions of the two points in the referential associated with sensor 17 are determined based on a measurement of the position of unit 21 with respect to unit 12 which defines a fixed referential with respect to the locator. The operation is repeated by engaging rod 22 into rod 5. These two series of measurements enable determining, in the referential defined by unit 12, and thus in the referential associated with the locator, the respective directions of rods 4 and 5. By mathematically readjusting the measured positions with a geometrical model of the rods or directly with the points of the rods determined on the scanner cross-sections, the transfer matrix between the referentials defined by guide mark 3 in the three-dimensional images reconstructed based on the scanner cross-sections and the locator referential can then be determined.

As an alternative, the additional step consists of engaging rod 22 into a rod (for example, 4) of guide mark 3 and of performing several orientation measurements on rod 22 by rotating it inside rod 4. This operation is repeated by rotating rod 22 inside rod 5. Then, the invariant axis of all the measurements performed for each of rods 4 and 5 in the referential defined by unit 12 is searched. This invariant axis corresponds to the direction of rod 4, respectively 5, in this referential and the intersection of the two obtained axes provides the origin of the referential associated with guide mark 3. The transfer matrix between the referential associated with guide mark 3 and the locator referential is deduced therefrom.

Knowing the different relations between referentials, the displacement to be applied to the relative positions of the jaws in the three-dimensional image processing system can now be simulated. After simulating the respective osteotomies of the bone segments of the mandible and of the maxilla with respect to the rest of the skull by isolating in the three-dimensional scanner images a portion corresponding to the maxilla and a portion corresponding to the mandible, the final position to be given to the mandible and to the maxilla can be simulated by means of the image processing system, independently from the initial interscupidation plate. Indeed, the respective positions of the mandible and of the maxilla are perfectly determined in the image processing system. Thus, the application, in the scanner images, of the relation between the initial and final referentials of the maxilla determined by the optical locator, enables obtaining a corrected maxillo-mandibular block, that is, in the position corresponding to that defined by the final interscupidation plate.

As an alternative (not shown), the optical localization device may be replaced with a video localization device using several cameras (stereovision) to localize the units respectively associated with mandible casting 11, with maxilla casting 14, and with interscupidation plate 1. In this case, the units of definition of three referentials are, for example, formed of graphic patterns locatable in position and orientation by an analysis of the video camera images. Physical guide mark 3 can here directly define a referential linked to the localization device. A same referential is then available on the scanner side and on the locator side. The same principle also applies to a locator by ultrasonic emitters or by electromagnetic sensors.

An advantage of the present invention is that an accurate tool of three-dimensional simulation of the surgical intervention to be performed without it being necessary to rigidly attach elements to the patient's skull is now available for the surgeon. In particular, the relative displacement between the maxilla and the mandible can be taken into account in a simulation and in a complete cephalometric analysis using the three-dimensional scanner images.

Another advantage of the present invention is that the exact knowledge of the respective positions and orientations of the different bone segments enables providing, within the operatory block, robotized surgery assistance means, the mandible and the maxilla being very accurately positionable by means of a robot, or by means of a passive guiding system, with respect to the patient's skull in the desired final position.

The positions are then given, for example, by means of a fixed optical locator in the operatory block and of interscupidation plate 1 put in the patient's mouth just before the operation. A new step of determination of the position of plate 1 enables transferring all the simulation data into the new referential associated with the optical locator. This step may be performed as previously by means of reference element 20. As an alternative, guide mark 3 may also be associated with a third diode unit (not shown) rigidly coupled to rods 4 and 5. This unit then defines a three-dimensional referential associated with plate 1 in the localization device.

It should be noted that, in the case of a manual positioning of the different bone segments, an interscupidation plate which determines the displacement of the maxilla with respect to the mandible in its original position is always made. In the case of a robotized positioning of the bone segments, the use of such an intermediary interscupidation plate is no longer necessary and the two jaws can be simultaneously repositioned.

It should also be noted that the present invention can also be implemented in the case where the maxilla must be divided into several fragments to obtain a correct dental positioning. In this case, several units 15 respectively associated with each fragment are used and a displacement matrix in the locator referential, then in the scanner referential, is determined for each assembly thus formed (casting fragment and diode unit).

According to a second embodiment of the present invention, the locator is used to implement the first step described in relation with FIG. 2 as well as the additional step (FIG. 4) of determination of the transfer matrix between the referential associated with guide mark 3 and the locator referential. However, the relative position between the two dental castings in the desired postoperative position is directly determined by means of the image processing system, without using a second interscupidation plate (16, FIG. 3). For this purpose, the surfaces of the two castings are digitized by means of a surface sensor, to obtain digital prints in the image processing system. The desired definitive positions between the jaws are then directly determined in the image processing system in which the initial positions are known accurately by the use of the locator and of first plate 1 associated with guide mark 3.

An advantage of this embodiment is that it enables using a computer system to optimize the positioning criteria and reliably and semi-automatically fulfil positioning constraints. Another advantage is that any processing relative to the simulation and to the determination of the definitive position of the jaws can here be performed by the surgeon whereas the final interscupidation plate is generally made by a dental technician based on data provided by the surgeon.

Of course, the present invention is likely to have various alterations, modifications and improvements which will readily occur to those skilled in the art. In particular, the realization of the computer tools and of the programs of calculation of the different relationships between the referentials is within the abilities of those skilled in the art based on the functional indications given hereabove.

What is claimed is:

1. An interscupidation plate (1) for defining an occlusion between two, respectively mandibular (11) and maxillary (14), dental castings, including, protruding from its front end, a guide mark (3) visible by means of an X-ray scanner and adapted to defining a first referential in three-dimensional images reconstructed from scanner views, said guide mark formed of at least two hollow rods connected to said interscupidation plate, said rods open at an end distal from said interscupidation plate.

2. The interscupidation plate of claim 1, wherein the guide mark (3) has at least two non-parallel rectilinear edges.

3. The interscupidation plate of claim 1 or 2, wherein said at least two rods (4, 5) connected to the interscupidation plate (1) together form a determined angle (α).

4. A device for determining a three-dimensional displacement between first and second relative positions of two dental castings for use with a localization device, said device for determining three-dimensional displacement including:
   a first unit (12), associated with a first dental casting (11) and locatable in position and orientation by the localization device (17);
   a second unit (15), associated with a second dental casting (14) and locatable by the localization device;
   a first interscupidation plate (1) defining the first relative position between the two castings (11, 14), the first plate (1) being locatable by the localization device (17);
   means for storing the position of the second unit (15) with respect to the first unit (12) when the relative position of the castings (11, 14) is determined by the first interscupidation plate (1);
   means for defining (16) the second relative position of the castings (11, 14); and
   calculation means adapted to determining the three-dimensional displacement of the second unit (15) between the two positions.

5. The device for determining a three-dimensional displacement of claim 4, wherein the means for defining the second relative position of the castings (11, 14) are formed of a second interscupidation plate (16), and further including:
   means for storing of the relative position of the second unit (15) with respect to the first unit (12) when the position of the castings (11, 14) is determined by the second interscupidation plate (16); and
   calculation means adapted to determining the three-dimensional displacement of the second unit (15) between the two positions.

6. The device for determining a three-dimensional displacement of claim 4 wherein the means for defining the second relative position of the castings (11, 14) comprise a device for digitizing the surfaces of the castings and image processing means.

7. The device for determining a three-dimensional displacement of claim 4, wherein the first interscupidation plate includes, protruding from its front end, a guide mark (3) visible by means of an X-ray scanner and adapted to defining a first referential in three-dimensional images reconstructed from scanner views, said guide mark formed of at least two hollow rods connected to said interscupidation plate, said rods open at an end distal from said interscupidation plate.

8. The device for determining a three-dimensional displacement of claim 4, wherein the localization device is formed of an optical locator (17), the locatable units (12, 15, 21) including infrared-emitting diodes (23).

9. The device for determining a three-dimensional displacement of claim 4, wherein the localization device (17) is formed of several video cameras associated with image processing means locatable units being formed of graphic patterns.

10. A system for simulating an orthognatic surgery action, including:
   an X-ray scanner;
   device (17) of three-dimensional localization of relative positions of dental castings (11, 14), each associated with a unit (12, 15) locatable in position and orientation by the localization device 17);
   means to determine a relation between a first referential associated to the tomographic images and a second referential associated to the localization device; and
   an image processing system for combining tomographic images provided by the scanner with positioning data provided by the localization device (17) to obtain three-dimensional images.

11. The simulation system of claim 10, wherein the localization device (17) is part of a device for determining a three-dimensional displacement between first and second relative positions of the two dental castings (11, 14) said device for determining a three-dimensional displacement including a first unit (12) associated with a first dental casting (11) and locatable in position orientation by a localization device (17); a second unit (15) associated with a second dental casting (14) and locatable by the localization device; a first interscupidation plate (1) defining the first relative position between the two castings (11, 14), the first plate (1) being locatable by the localization device (17); means for storing the position of the second unit (15) with respect to the first unit (12) when the relative position of the castings (11, 14) is determined by the first interscupidation plate (1); means for defining (1) the second relative position of the castings (11,14); and calculation means adapted to determining the three-dimensional displacement of the second unit (15) between the two positions.

12. The simulation system of claim 11, wherein a first position is determined by a first interscupidation plate (1) for defining an occlusion between two, respectively mandibular (11) and maxillary (14), dental castings, including, protruding from its front end, a guide mark (3) visible by means of an X-ray scanner and adapted to defining a first referential in three-dimensional images reconstructed from scanner views, said guide mark formed of at least two hollow rods connected to said interscupidation plate, said rods open at an end distal from said interscupidation plate.

13. The simulation system of claim 12, wherein the relation between the first and second referentials is determined from an additional unit (21) of a reference element (20) adapted to being mechanically associated to the guide mark (3) of the first interscupidation plate (1).

14. The simulation system of claim 12, wherein the guide mark (3) of the first interscupidation plate (1) is rigidly coupled with a third locatable unit which defines a second referential associated with the first plate (1).

15. The system of claim 12, wherein said localization device is a localizator having no mechanical connection between the localized elements.

* * * * *